US012740731B2

(12) United States Patent
Bootz

(10) Patent No.: US 12,740,731 B2
(45) Date of Patent: Sep. 22, 2026

(54) SAFETY UNIT FOR ANALYTE SENSOR

(71) Applicant: Roche Diabetes Care, Inc., Indianapolis, IN (US)

(72) Inventor: Felix Bootz, Speyer (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 206 days.

(21) Appl. No.: 18/808,163

(22) Filed: Aug. 19, 2024

(65) Prior Publication Data

US 2024/0407680 A1 Dec. 12, 2024

Related U.S. Application Data

(63) Continuation of application No. PCT/EP2023/054120, filed on Feb. 20, 2023.

(30) Foreign Application Priority Data

Feb. 22, 2022 (EP) .................................... 22157945

(51) Int. Cl.

*A61B 5/00* (2006.01)
*A61B 5/145* (2006.01)
*A61B 5/1473* (2006.01)

(52) U.S. Cl.

CPC .......... *A61B 5/1473* (2013.01); *A61B 5/0002* (2013.01); *A61B 5/14532* (2013.01); *A61B 5/6849* (2013.01)

(58) Field of Classification Search

CPC ... A61B 5/145; A61B 5/14532; A61B 5/1473; A61B 5/002; A61B 5/14846;

(Continued)

(56) References Cited

U.S. PATENT DOCUMENTS 9,662,070 B2 * 5/2017 Roesicke ........... A61B 5/14532
2009/0076355 A1 3/2009 Reggiardo (Continued)

FOREIGN PATENT DOCUMENTS

WO WO 01/36660 A2 5/2001

OTHER PUBLICATIONS

International Preliminary Report on Patentability, PCT/EP2023/054120, Aug. 27, 2024, 6 pages.

(Continued)

*Primary Examiner* — Chu Chuan Liu
(74) *Attorney, Agent, or Firm* — Bose McKinney & Evans LLP

(57) ABSTRACT

Analyte sensor for use in medical devices for measuring analyte data such as glucose data, including: a power source providing electrical power to the analyte sensor, an enclosure of the analyte sensor, a sensor circuit powered by the power source and including two electrodes, wherein the electrodes each have a first portion that lies inside the enclosure and a second portion that lies outside of the enclosure. At least one protection unit is electrically coupled to the first portion of each of the two electrodes located inside the enclosure, wherein the at least one protection unit is configured to short-circuit the two electrodes in case a voltage signal from the sensor circuit applied to the electrodes exceeds a predetermined voltage threshold. A method for operating an analyte sensor is also disclosed.

13 Claims, 3 Drawing Sheets

(58) Field of Classification Search
CPC ... A61B 5/6833; A61B 5/6849; A61B 5/7225; A61B 2562/18; A61B 2562/182
See application file for complete search history.

(56) References Cited

U.S. PATENT DOCUMENTS

| | | | |
|---|---|---|---|
| 2017/0181672 A1 | 6/2017 | Nogueira et al. | |
| 2019/0378615 A1 * | 12/2019 | Martin | A61B 5/6833 |
| 2021/0030339 A1 | 2/2021 | Huang et al. | |

OTHER PUBLICATIONS

International Search Report and Written Opinion, PCT/EP2023/054120, May 4, 2023, 8 pages.

Feldman et al., Diabetes Technology & Therapeutics, v5(5), p. 769-779, 2003.

* cited by examiner

Figure 3:
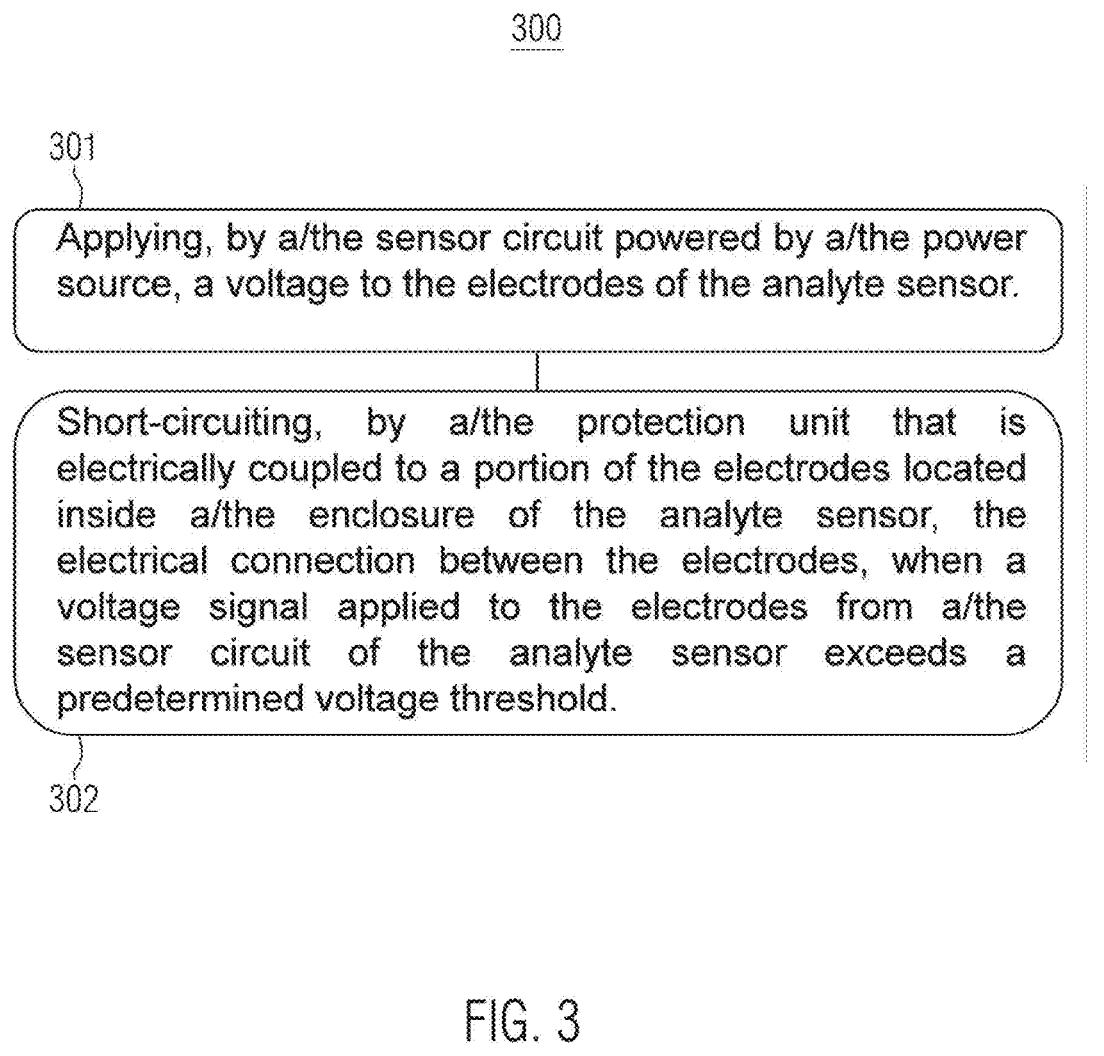

300

301

Applying, by a/the sensor circuit powered by a/the power source, a voltage to the electrodes of the analyte sensor.

Short-circuiting, by a/the protection unit that is electrically coupled to a portion of the electrodes located inside a/the enclosure of the analyte sensor, the electrical connection between the electrodes, when a voltage signal applied to the electrodes from a/the sensor circuit of the analyte sensor exceeds a predetermined voltage threshold.

SAFETY UNIT FOR ANALYTE SENSOR

CROSS REFERENCE TO RELATED APPLICATIONS

This is a continuation of PCT/EP2023/054120 filed Feb. 20, 2023 which claims priority from EP 22 157 945.1 filed Feb. 22, 2022 the disclosures of both of which are incorporated herein by reference.

BACKGROUND

State of the Art

The present disclosure relates to the power management of portable electronic medical sensor devices, such as a wearable on-body analyte sensor of a continuous analyte monitoring system that, for example, can be worn or carried by a user to monitor his analyte levels, e.g., his glucose levels.

A common type of analyte sensor exploits the fact that certain electrochemical reactions of an analyte to be detected or to be measured can generate electrical signals, e.g., electric currents or electric potentials, that can correlate with the concentration of the analyte to be detected, e.g., that are directly or indirectly proportional to the concentration of the analyte. For example, voltammetric or amperometric analyte sensors can measure a current response between a working electrode and a reference electrode in order to measure analyte levels.

Such analyte sensors are, for example, commonly used for measuring glucose levels, and in particular can be part of in-vivo continuous glucose monitoring systems that measure glucose levels in the blood and/or in interstitial fluids of patients suffering from diabetes.

During the operation of such analyte sensors for taking analyte measurements, the electrodes of the analyte sensor are partially inserted into the skin of the patient, i.e., are partially immersed in body fluid of the patient, and when a voltage is applied to the electrodes of the analyte sensor a current is generated in the patient that flows between the electrodes of the analyte sensor.

While the currents flowing between the electrodes of the analyte sensor are in general not harmful for the patient, it is important that the analyte sensor is safe to use at all times, even in cases where the analyte sensor is malfunctioning.

Common means to prevent harm to a patient caused by malfunctioning analyte sensors are not always fully reliable and/or require a lot of space and a large number of components, thereby making the analyte sensors more bulky and more heavy, and/or are too intricate and/or complicate the manufacturing process of analyte sensors.

SUMMARY

The present disclosure provides means for improving the safety of analyte sensors.

In particular, the present disclosure provides a safe-to-use, simplified, more compact, more cost-effective, and more reliable electrochemical analyte sensor that, inter alia, can be used in a continuous analyte, e.g. glucose, monitor system.

Advantageous embodiments and further developments are disclosed throughout the specification.

For example, an electronic analyte sensor for use in medical devices, in particular portable, e.g., wearable/on-body, electronic medical devices, for measuring analyte data, in particular for measuring glucose data, may comprise one, some or all of the following components:

- at least one power source/power supply, e.g., a battery, for providing electrical power to the analyte sensor,
- an enclosure of the analyte sensor,
- a sensor circuit powered by said at least one power source, the sensor circuit comprising at least two electrodes, wherein said electrodes each have a first portion that lies inside the enclosure and a second portion that lies outside of the enclosure,
- at least one protection unit, wherein said at least one protection unit is electrically coupled to the first portion of each of the two electrodes, i.e., the portion of each of the two electrodes that is located inside the enclosure, and wherein said at least one protection unit is configured to short/short-circuit the electrodes/the two electrodes in case a voltage signal from/originating from/occurring in the sensor circuit and applied to the electrodes exceeds a predetermined voltage threshold.

Said portions of the electrodes that are located within the enclosure of the analyte sensor do not come into direct physical contact with the body/skin of a user/patient when the analyte sensor is taking analyte measurements of a user/patient. The at least one protection unit can therefore be configured to short-circuit the electrodes between said (first) portions of the electrodes that are located within the enclosure of the analyte sensor.

Hence, when a voltage signal from/originating from/occurring in the sensor circuit exceeds a predetermined voltage threshold, the electrodes are shorted/short-circuited outside the body of a user/patient.

Only the second portions or end portions of the electrodes that are located outside the enclosure of the analyte sensor are configured for transcutaneous analyte measurements, i.e., are configured to be in direct physical contact with the body/skin of a user/patient, i.e., are configured to be inserted into the body of a user/patient for taking the analyte measurements.

The above and herein exemplary described analyte sensor provides a more robust, more compact, more reliable, less intricate and more cost-effective way to improve the safety of use of the analyte sensor and thereby the safety of a user/patient, since it is prevented that any harmful electric voltages enter the body of a user/patient.

The above and herein exemplary described protection unit of the analyte sensor can act as an electrically operable switch that closes the electric circuit of the analyte sensor within the enclosure of analyte sensor, so that no current can flow between the second portions/end portions of the electrodes that are located outside of the enclosure of the analyte sensor.

The above and herein exemplary described analyte sensor design and configuration, inter alia, allow also to dispense with the need for equipping the analyte sensor with a large number of current or voltage delimiting components that are normally needed to provide further safety by redundancy and that can take a significant amount of space.

Stated differently, the above and herein exemplary described analyte sensor design and configuration, inter alia, can reduce the space needed on a printed circuit board that can carry the sensor circuit and other electronic components of the analyte sensor, thereby reducing size, weight and manufacturing costs of the analyte sensor.

The possibility of reducing the number of electronic components of the analyte sensor also makes the analyte sensor more robust and less error prone since the complexity of the analyte sensor is reduced.

The above and herein exemplary described analyte sensor design and configuration also do not require that the energy supply to the sensor circuit from the power supply is interrupted.

The safety of the patient/user is ensured by the above and herein exemplary described analyte sensor at all times and any damage to the analyte sensor/the sensor circuit of the analyte sensor that may occur as a consequence of shorting/short-circuiting the electrodes by the at least one protection unit is condoned.

Stated differently, the above and herein exemplary described analyte sensor design and configuration can be used to dispense with the need for controlling and/or interrupting the power supply to the sensor circuit of the analyte sensor to protect the sensor circuit components.

The above and herein exemplary described predetermined voltage threshold(s) can, for example, be determined/chosen on the basis of the voltage used in/of the at least one power source/power supply of the analyte sensor. For example, possible predetermined voltage threshold(s) may lie at around 3.25 V or above, albeit also other lower predetermined voltage thresholds are conceivable too.

Furthermore, additional concerns regarding the patient safety, for example, specific patient conditions, e.g., such as age and/or health conditions, may also provide a basis for determining said predetermined voltage threshold(s).

The at least one protection unit may be an electrically operable switch/may be configured as an electrically operable switch/may comprise at least one electrically operable switch.

The at least one protection unit/the at least one electrically operable switch may, for example, comprise at least one transistor and/or at least one thyristor, e.g., a solid-state semiconductor unit with four layers of alternating P- and N-type materials, and/or at least one solid-state relay.

For example, a transistor of the at least one protection unit/transistor of the at least one electrically operable switch may be a bipolar junction transistor.

A base of a transistor of the least one protection unit/the least one electrically operable switch can be electrically coupled to one of the electrodes via at least one resistor.

Stated differently, the at least one protection unit/the at least one electrically operable switch may, for example, comprise at least one transistor and at least one resistor.

Furthermore, the analyte sensor can be configured for being removably attached to a mounting unit for placing the analyte sensor on the skin of a user and for maintaining the analyte sensor in position. Stated differently, the analyte sensor can be reusable, i.e., it can be attached and removed from the skin of a user many times.

The mounting unit may further comprise an inserting element, e.g., a cannula, configured for facilitating the guiding of the end portions of the electrodes of the analyte sensor during partial insertion of the electrodes into the skin/body of the user for taking analyte measurements.

Said exemplary mounting unit can be implemented as a patch unit that can be configured to be removably attached to the skin/body of a user and that can be configured to receive and hold the analyte sensor such that the analyte sensor can perform analyte measurements of the user over a period of time while being coupled to the user via the mounting unit/patch unit.

However, it is also conceivable that the mounting unit or patch unit is integrated in the analyte sensor.

To facilitate attaching the mounting unit/patch unit at least temporarily and removably on the skin of a user and for maintaining the analyte sensor in position, the mounting unit/patch unit may comprise a plaster/an adhesive/adhesive means/an adhesive layer on its lower surface.

It is also possible that the at least one mounting unit/patch unit is configured as a plaster/an adhesive layer/adhesive means.

The analyte sensor may comprise a digital communication interface configured for transmitting, e.g., wirelessly, data measured by the analyte sensor to a data analysis unit, e.g., a data analysis unit of a continuous analyte, e.g., glucose, monitor system.

However, the analyte sensor itself may comprise one or more processors for analyzing data, e.g., glucose data, measured by the analyte sensor.

The analyte sensor may also comprise means for outputting analyte data, e.g., glucose data, measured by the analyte sensor and/or data derived from the measured analyte data and/or further other data via visual and/or audible and/or tactile indications.

For example, the analyte sensor may comprise a display for displaying measured data, e.g., measured glucose data, and other information.

One of the electrodes of the herein described analyte sensor can be a working electrode and the other electrode of the analyte sensor can be an electrode selected from a group comprising the following types: a counter electrode and a combined counter/reference electrode and/or wherein said other electrode comprises gold or platinum.

It is possible that the herein exemplary described analyte sensor may comprise no more than two electrodes, e.g., may comprise exactly two electrodes, i.e., exactly one working electrode and exactly one other electrode, e.g., a counter electrode or a combined counter/reference electrode. However, it is also conceivable that the herein exemplary described analyte sensor may comprise more than two electrodes, e.g., three or four or more electrodes.

The first electrode may comprise only one enzyme or a mixture of two or more enzymes. Only one enzyme is preferred. Specifically, the enzyme is capable of catalyzing a chemical reaction converting the analyte, in particular glucose. Even more specifically, the at least one enzyme is selected from the group consisting of a glucose oxidase (EC 1.1.3.4), a hexose oxidase (EC 1.1.3.5), an(S)-2 hydroxy acid oxidase (EC 1.1.3.15), a cholesterol oxidase (EC 1.1.3.6), a glucose dehydrogenase, a galactose oxidase (EC 1.1.3.9), an alcohol oxidase (EC 1.1.3.13), an L-glutamate oxidase (EC 1.4.3.11), and an L-aspartate oxidase (EC 1.4.3.16). In particular, the at least one enzyme is a glucose oxidase (GOx) and/or modifications thereof.

The at least one enzyme may be comprised in a sensing material. The term "sensing material", as used herein, specifically may refer, without limitation, to a material that may be or may comprise at least a polymeric material; specifically, it may be or may comprise at least a polymeric material and at least a metal containing complex. The metal containing complex may be selected from the group consisting of transition metal element complexes; specifically, the metal containing complex may be selected from osmium-complexes, ruthenium-complexes, vanadium-complexes, cobalt-complexes, and iron-complexes, such as ferrocenes, such as 2-aminoethylferrocene. Even more specifically, the sensing material may be a polymeric transition metal complex as described for example in WO 01/36660 A2, the content of which is included by reference. In particular, the sensing material may comprise a modified poly(vinylpyridine) backbone loaded with poly(bi-imidizyl) Os complexes covalently coupled through a bidentate linkage. A suitable sensing material is further described in Feldmann et al, Diabetes Technology & Therapeutics, 5 (5), 2003, 769-779, the content of which is included by reference. Suitable sensing materials further may include ferrocene-containing polyacrylamide-based viologen-modified redox polymer, pyrrole-2,2'-azino-bis(3-ethylbenzthiazoline-6-sulfonic acid)(ABTS)-pyrene, Naphthoquinone-LPEI. The polymeric transition metal complex may represent a redox mediator incorporated into a cross-linked redox polymer network. This is advantageous as it may facilitate electron transfer between the at least one enzyme or analyte and the conductive trace. In order to avoid a sensor drift, the redox mediator and the enzyme may be covalently incorporated into a polymeric structure.

In an embodiment the sensing material may comprise a polymeric material and MnO2-particles or any other material catalyzing hydrogen peroxide oxidation reaction as well as the at least one enzyme. Another material catalyzing hydrogen peroxide oxidation reaction is Pt (platinum).

Moreover, the sensing material may additionally comprise at least one crosslinker; the crosslinker may, for example, be capable of crosslinking at least part of the sensing material.

An exemplary continuous analyte, e.g., glucose, monitor system may comprise a medical device comprising an analyte sensor as described herein and one or more processors configured for processing data collected by the analyte sensor.

Said exemplary continuous analyte, e.g., glucose, monitor system may further comprise means for outputting analyte data, e.g., glucose data, measured by the analyte sensor and/or data derived from the measured analyte data and/or further other data via visual and/or audible and/or tactile indications.

For example, the exemplary continuous analyte, e.g., glucose, monitor system may comprise a display for displaying data, e.g., glucose data, measured by the analyte sensor and/or a loud speaker that can output audible information and feedback on data, e.g., glucose data, measured by the analyte sensor.

An exemplary kit may, for example, comprise one, some or all of the following components:

- at least one analyte sensor, as exemplarily described herein, and
- at least one mounting unit/skin adherable skin mounting unit, e.g., a patch unit, configured for the placement of the at least one analyte sensor on the skin of a user and to which the at least one analyte sensor can be detachably coupled,
- at least one inserter unit/device, wherein said at least one inserter unit can comprise a needle and wherein the at least one inserter unit can be configured for enabling placement/at least partial insertion of the needle in a cutaneous or subcutaneous region of a user/patient.

The at least one mounting unit/patch unit may comprise at least one plaster/adhesive layer/adhesive/adhesive means, e.g., provided on/glued to its lower surface/bottom surface, i.e., on a surface that can come into contact with the skin of a user/patient.

It is also possible that the at least one mounting unit/patch unit is configured as a plaster/an adhesive layer/adhesive means.

In addition/alternatively, at least one plaster/adhesive layer/adhesive means may be glued to/provided on a lower surface/bottom surface of an enclosure/housing of the at least one analyte sensor.

Furthermore, the at least one inserter unit may be configured for accommodating the at least one analyte sensor, i.e., the at least one analyte sensor can be coupled/removably attached to the at least one inserter unit. For example, the at least one inserter unit may comprise a chamber in which the at least one analyte sensor can be positioned and accommodated.

The inserter unit can be configured as a sterile packaging for the analyte sensor and may, for example, comprise a sterile cap on its lower surface/bottom surface that can be removed before a needle of the inserter unit at a chosen insertion site can be placed/inserted in a cutaneous or subcutaneous region of a user/patient.

The at least one inserter unit/device can be disposable or reusable. However, even if the inserter unit/device is designed as a disposable unit, the at least one analyte sensor can be designed for reuse and can be detached from the inserter unit/device for further use with another inserter unit/device.

For example, after insertion, the inserter unit can be removed from the insertion site thereby separating/detaching the inserter unit from the analyte sensor that can stay in place/fixed at the insertion site via the mounting unit/plaster/adhesive layer/adhesive means.

All the exemplary components of the exemplary kit may be provided in the kit in disassembled and/or in partially assembled and/or in fully assembled manner.

While the at least one analyte sensor may comprise an integral internal communication interface configured for transmitting data to a data analysis unit, e.g., an external data analysis unit, e.g., a smartphone, the kit may also further comprise a communication interface configured for transmitting data, wherein said communication interface can be removably attached to the at least one analyte sensor.

An exemplary method of operating an analyte sensor as exemplarily described herein may comprise one, some or all of the following exemplary steps:

- applying, by a/the sensor circuit powered by a/the power source, a voltage to the electrodes of the analyte sensor, and
- short-circuiting, by a/the protection unit that is electrically coupled to a portion of the electrodes located inside a/the enclosure of the analyte sensor, the electrical connection between the electrodes within the enclosure of the analyte sensor, when a voltage signal applied to the electrodes by/via/from a/the sensor circuit of the analyte sensor exceeds a predetermined voltage threshold. Stated differently, the electrodes can be shorted/short-circuited by a/the protection unit, e.g. by an electrically operable switch, within the enclosure of the analyte sensor and outside the body of a user/patient.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein:

FIG. 3 is an exemplary flow diagram of a method for the operation of an analyte sensor.

Figure 1:
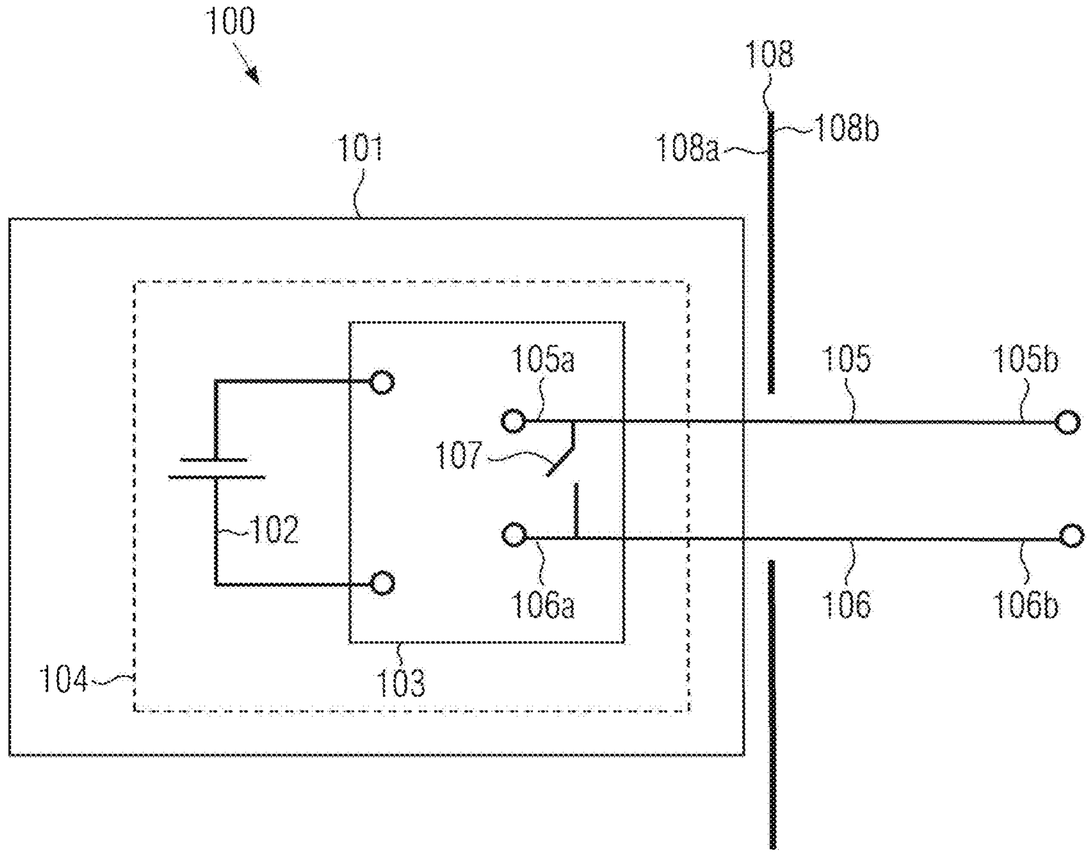
FIG. 1 is a schematic view of an exemplary analyte sensor.

Corresponding reference characters indicate corresponding parts throughout the several views. Although the exemplification set out herein illustrates embodiments of the invention, in several forms, the embodiments disclosed herein are not intended to be exhaustive or to be construed as limiting the scope of the invention to the precise forms disclosed.

DETAILED DESCRIPTION

FIG. 1 exemplarily shows a schematic overview of an analyte sensor 100 that may comprise one, some or all of the above exemplary described features.

For example, the analyte sensor 100 comprises a power source 102, e.g., a battery, that can supply the electronic components of the analyte sensor with electric power. In particular, the exemplary power source 102 can provide electric power to the exemplary sensor circuit 103 of the analyte sensor.

The exemplary sensor circuit 103 can comprise two electrodes 105, 106, wherein the electrodes each have a first portion 105*a*, 106*a* that lies inside/within the enclosure 101 and a second portion 105*b*, 106*b* that lies outside of the enclosure 101 of the analyte sensor.

All or the majority of electronic components of the analyte sensor, i.e., including the power source 102, the sensor circuit 103, the protection unit 107, and the first portion(s) 105*a*, 106*a* of the electrodes 105, 106, can be mounted on/can be carried by/can be coupled to each other by the exemplary printed circuit board 104.

The exemplary analyte sensor 100 further comprises an exemplary protection unit 107, wherein said protection unit 107 is electrically coupled to the portion 105*a*, 106*a* of each of the two electrodes 105, 106 that is located inside the enclosure 101 of the analyte sensor.

Thereby the exemplary protection unit 107 can be configured to short-circuit the two electrodes 105, 106 in case a voltage signal from the sensor circuit 103 applied to the electrodes 105, 106 exceeds a predetermined voltage threshold.

Stated differently, the exemplary protection unit 107 can act as an electrically operable switch or can comprise an electrically operable switch that closes the electric circuit comprising the two electrodes at a location within the enclosure of the analyte sensor 100.

In other words, the exemplary protection unit 107 can electrically couple the first portions 105*a*, 106*a* of the electrodes 105, 106 that lie inside/within the enclosure (not shown) of the analyte sensor, e.g. on the exemplary printed circuit board 104.

However, in the exemplary shown state, the protection unit 107 has not been triggered to short-circuit the two electrodes, i.e., the switch is open.

Hence, in the shown case, the analyte sensor 100 would be able to perform analyte measurements when the second portions/end portions 105*b*, 106*b* of the electrodes 105, 106 would be brought into contact with body fluid/body tissue of a user/patient such that, when a voltage is applied to the electrodes 105, 106, a current would flow between the end portions 105*b*, 106*b* of the electrodes 105, 106 and the analyte measurements of the user/patient could be taken.

When the protection unit 107 is triggered to short-circuit the two electrodes (not shown), the switch would be in a closed state and no current would flow between the second portions/end portions 105*b*, 106*b* of the electrodes 105, 106, thereby preventing that any possible harmful currents/harmful voltages/harmful potential differences are applied to a user in contact with the second portions/end portions 105*b*, 106*b* of the electrodes 105, 106.

Further exemplarily illustrated is an exemplary mounting unit/patch unit 108 to which the analyte sensor 100 can be coupled and which allows the proper placement of the analyte sensor 100 on the body/on the skin of a user to partially insert the second portions/end portions 105*b*, 106*b* of the electrodes 105, 106 of the analyte sensor for taking analyte measurements.

In the shown exemplary orientation, the reference numeral 108*a* denotes the side/surface of the mounting unit/patch unit 108 facing the analyte sensor and the reference numeral 108*b* denotes the side/surface of the mounting unit/patch unit 108 facing the user/patient (not shown).

Figure 2:
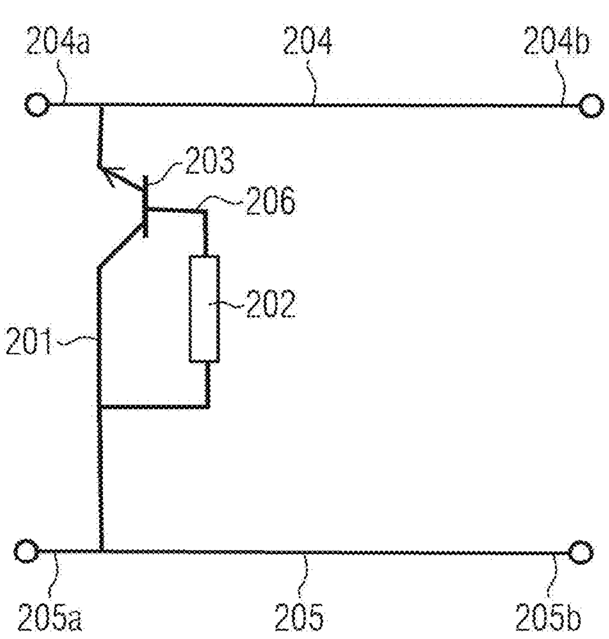
FIG. 2 is a schematic view of the implementation of an exemplary protection unit.

FIG. 2 shows a further exemplary implementation 200 of a protection unit 201 of an analyte sensor. For clarity, only the electrodes 204, 205 of the analyte sensor are shown. However, the components omitted for the sake of clarity, such as enclosure of the analyte sensor, power source, sensor circuit, printed circuit board, mounting unit are understood to be nevertheless present and are understood to be arranged, configured and oriented identical or analogously to the configuration of the analyte sensor 100 shown in FIG. 1.

In the shown example, the protection unit 201 is implemented as comprising a bipolar junction transistor 203, wherein the base 206 of the transistor is coupled to one of the electrodes 205 via a resistor 202.

As described previously, the coupling occurs between first portions 204*a*, 205*a* of the electrodes 204, 205 that lie inside/within the enclosure (not shown) of the analyte sensor.

For completeness, it is noted that the exemplary second portions/end portions 204*b*, 205*b* of the exemplary electrodes 204, 205 are understood to lie outside the enclosure (not shown) of the analyte sensor.

As described previously, when a voltage signal from the sensor circuit applied to the electrodes exceeds a predetermined voltage threshold, the protection unit 201 short-circuits the two electrodes 204, 205 by closing the electric circuit between the first portions 204*a*, 205*a* of the electrodes 204, 205 that lie inside/within the enclosure (not shown) of the analyte sensor.

FIG. 3 shows an exemplary flow diagram of a method, 300, of operating an analyte sensor with some or all of the features as exemplarily described above, wherein the method can comprise one, some or all of the following exemplary steps.

For example, in a first step, 301, a voltage can be applied to the electrodes of an analyte sensor by a sensor circuit of the analyte sensor which can be powered by a power source, e.g., a battery.

Subsequently, the method may comprise a step of short-circuiting, 302, by the protection unit of the analyte sensor that is electrically coupled to a portion of the analyte sensor electrodes located inside the enclosure of the analyte sensor, the electrical connection between the electrodes, when a voltage signal applied to the electrodes from the sensor circuit of the analyte sensor exceeds a predetermined voltage threshold.

In FIG. 1, FIG. 2 and FIG. 3, the reference signs denote the following exemplary aspects, exemplary components and exemplary steps.

100 Exemplary analyte sensor
101 Exemplary enclosure/casing of analyte sensor
102 Exemplary power source/power supply, e.g. battery
103 Exemplary sensor circuit
104 Exemplary printed circuit board
105 Exemplary first electrode, exemplary counter electrode/reference electrode

105*a* Exemplary first portion of first electrode that is located inside the enclosure

105*b* Exemplary second portion/end portion of first electrode that is located outside the enclosure

106 Exemplary second electrode, exemplary working electrode

106*a* Exemplary first portion of second electrode that is located inside the enclosure

106*b* Exemplary second portion/end portion of second electrode that is located outside the enclosure

107 Exemplary protection unit, exemplary electrically operable switch

108 Exemplary mounting unit

108*a* Exemplary side/surface of mounting unit facing the analyte sensor

108*b* Exemplary side/surface of mounting unit facing the user/patient

200 Exemplary and schematic protection unit implementation

201 Exemplary protection unit

202 Exemplary resistor

203 Exemplary transistor

204 Exemplary first electrode, exemplary counter electrode/reference electrode

204*a* Exemplary first portion of first electrode that is located inside the enclosure

204*b* Exemplary second portion/end portion of first electrode that is located outside the enclosure

205 Exemplary second electrode, exemplary working electrode

205*a* Exemplary first portion of second electrode that is located inside the enclosure

205*b* Exemplary second portion/end portion of second electrode that is located outside the enclosure

206 Exemplary base of transistor

300 Exemplary schematic flow diagram for a method of operating an analyte sensor

301, 302 Exemplary method steps

While this invention has been described as having an exemplary design, the present invention may be further modified within the spirit and scope of this disclosure. This application is therefore intended to cover any variations, uses, or adaptations of the invention using its general principles.

What is claimed is:

1. Analyte sensor for use in medical devices for measuring analyte data comprising:

a power source for providing electrical power to the analyte sensor;

an enclosure of the analyte sensor;

a sensor circuit powered by the power source and comprising two electrodes, wherein the electrodes each have a first portion disposed inside the enclosure and a second portion disposed outside of the enclosure;

at least one protection unit, wherein the protection unit is electrically coupled to the first portion of each of the two electrodes disposed inside the enclosure; and wherein the at least one protection unit is configured to short-circuit the two electrodes when a voltage signal from the sensor circuit applied to the electrodes exceeds a predetermined voltage threshold.

2. The analyte sensor according to claim 1, wherein the at least one protection unit comprises an electrically operable switch.

3. The analyte sensor according to claim 2, wherein the electrically operable switch comprises a transistor and/or a thyristor and/or a solid-state relay.

4. The analyte sensor according to claim 2, wherein the electrically operable switch comprises a transistor that is a bipolar junction transistor.

5. The analyte sensor according to claim 2, wherein the electrically operable switch comprises a transistor wherein a base of the transistor is coupled to one of the two electrodes via at least one resistor.

6. The analyte sensor according to claim 1, wherein the analyte sensor is configured for being removably attached to a mounting unit for placing the analyte sensor on the skin of a user.

7. The analyte sensor according to claim 1, comprising a communication interface configured for transmitting data measured by the analyte sensor to a data analysis unit.

8. The analyte sensor according to claim 1, wherein one of the two electrodes is a working electrode and the other one of the two electrodes is an electrode selected from a group comprising the following types: a counter electrode, a combined counter/reference electrode and an electrode comprising gold or platinum.

9. A continuous analyte monitoring system comprising:

a medical device comprising the analyte sensor according to claim 1; and one or more processors configured for processing data collected by the analyte sensor.

10. The system according to claim 9 comprising means for outputting analyte data measured by the analyte sensor and/or data derived from the measured analyte data via visual and/or audible and/or tactile indications.

11. A kit comprising:

the analyte sensor according to claim 1;

at least one mounting unit configured for the placement of the analyte sensor on the skin of a user and to which the analyte sensor can be detachably coupled, wherein the at least one mounting unit comprises plaster or adhesive.

12. The kit according to claim 11, further comprising:

at least one inserter unit, wherein the at least one inserter unit comprises a needle and is configured for enabling placement of the needle in a cutaneous or subcutaneous region of a user or a patient.

13. A method of operating the analyte sensor according to claim 1, comprising:

applying, with the sensor circuit powered by the power source, a voltage to the two electrodes of the analyte sensor;

short-circuiting, by the protection unit that is electrically coupled to the first portion of the electrodes disposed inside the enclosure of the analyte sensor, the electrical connection between the electrodes, when the voltage applied to the electrodes by the sensor circuit of the analyte sensor exceeds a predetermined voltage threshold.

* * * * *